(12) United States Patent
Pierre et al.

(10) Patent No.: US 8,720,220 B2
(45) Date of Patent: May 13, 2014

(54) AIR CONVECTION WARMER WITH NOISE REDUCTION FILTER

(75) Inventors: Joseph Pierre, Brockton, MA (US); Rachel Starr, Randolph, MA (US); David G. Roome, Honeoyoe, NY (US)

(73) Assignee: Smiths Medical ASD, Inc., Rockland, MA (US)

( * ) Notice: Subject to any disclaimer, the term of this patent is extended or adjusted under 35 U.S.C. 154(b) by 1563 days.

(21) Appl. No.: 11/798,974

(22) Filed: May 18, 2007

(65) Prior Publication Data

US 2008/0286092 A1  Nov. 20, 2008

(51) Int. Cl.
*F25D 19/00* (2006.01)

(52) U.S. Cl.
USPC .............................................. 62/296; 62/261

(58) Field of Classification Search
USPC ........ 62/261, 296; 181/225–226; 55/320–322
See application file for complete search history.

(56) References Cited

U.S. PATENT DOCUMENTS

| | | | | |
|---|---|---|---|---|
| 2,968,359 A * | 1/1961 | Cocker | ........................ | 181/236 |
| 3,811,251 A * | 5/1974 | Gibel | ............................. | 96/381 |
| 5,313,803 A * | 5/1994 | Detzer | .............................. | 62/89 |
| 5,733,320 A | 3/1998 | Augustine | | |
| 5,836,813 A * | 11/1998 | Miyata et al. | ................. | 454/139 |
| 6,126,393 A | 10/2000 | Arnold | | |
| 6,254,337 B1 * | 7/2001 | Arnold | ......................... | 415/119 |
| 6,892,851 B2 * | 5/2005 | Lee | ................................ | 181/224 |
| 7,037,068 B2 * | 5/2006 | Cobb et al. | .................... | 415/119 |
| 7,431,127 B2 * | 10/2008 | de Borchgrave et al. | ..... | 181/229 |

* cited by examiner

*Primary Examiner* — Cassey D Bauer
(74) *Attorney, Agent, or Firm* — Louis Woo

(57) ABSTRACT

To reduce the noise level of air convective warmer, the air filter of the warmer is fitted with an air intercept mechanism to disrupt the flow of air that traverses inside the interior cavity of the air filter. By thus disrupting the air flow, the noise that otherwise would have been generated due to a non-interrupted air stream flow is lowered. The air intercept mechanism may be in the form of at least one partition positioned inside the interior cavity of the air filter. Alternatively, double-ended open tubes may be used, so long as the interior cavity of the filter is sealed, with only the tubes providing the passages for air to output from the air filter. Yet a third embodiment of the air reduction filter has an air impermeable material covering at least one portion of the surface area of the filtering material to prevent the inflow air from directly entering into the interior cavity of the air filter through the covered surface area.

20 Claims, 4 Drawing Sheets

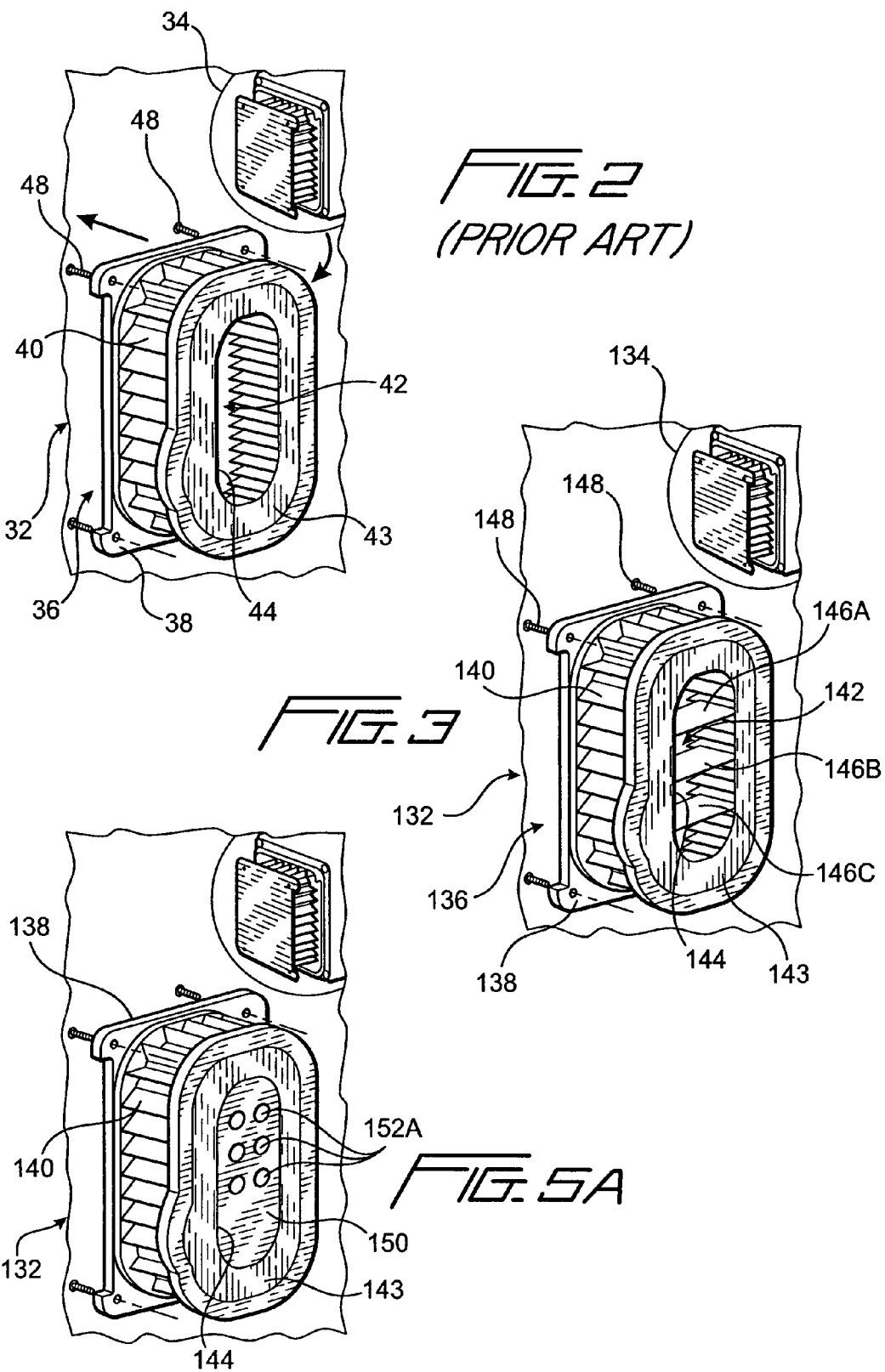

AIR CONVECTION WARMER WITH NOISE REDUCTION FILTER

FIELD OF THE INVENTION

The instant invention relates to air convection warmers and more particularly to an air convection warmer that operates at a lower noise level and yet produces the same throughput of temperature regulated air to inflate a convective blanket.

BACKGROUND OF THE INVENTION

To regulate the body temperature of a patient so as to prevent hypothermia in the patient, a convective blanket that provides a constant stream of warmed air to the patient is used. Convective blankets are inflated by air convective warmers. Most, if not all, air convective warmers produce a high level of noise, at least for some of the patients and others who may be close to the machine. This is because blowers are utilized in the convective warmers to propel a stream of air, heated or otherwise, from an air inlet to an air outlet, in order to inflate the convective blanket. The noise from the blower, along with the air stream flow through the convective warmer, tend to produce substantial noise. Such substantial noise could be an annoyance to the patient. The noise from the air convective warmer therefore needs to be reduced.

Prior to the instant invention, attempts have been made to reduce the noise of air convective warmers. Such attempts include U.S. Pat. No. 6,126,393 and its related U.S. Pat. No. 6,254,337. These patents disclose the configuration of an air blower unit in which the air inlet is pointed toward the surface onto which the housing of the air blower unit rests. The outlet for the air blower is provided at a side of the housing, and is coupled to an air hose that has an elbow bent between 45° and 90°. Thus configured, noise generated by the warmer allegedly is absorbed by the elbow, and the noise waves that are not absorbed by the elbow are allegedly reflected downwardly onto the support surface by the elbow.

Another attempt to reduce the noise of an air blower is disclosed in U.S. Pat. No. 5,733,320. In the '320 device, noise cancellation components are used. Such noise canceling components include an input sensor such as a microphone, a sound source such as a loud speaker, a noise cancellation controller and an optional error microphone. An audio noise cancelling signal, 180° out of phase with the noise measured by the input microphone, is output from the loudspeaker to cancel out the noise.

Yet another attempt to reduce the noise level of an air convective warmer is disclosed in U.S. Pat. No. 7,037,068, assigned to the assignee of the instant application. In the '068 device, indentations are provided at the interior surface of the plenum chamber of the warmer to suppress the noise. The disclosure of the '068 patent is incorporated by reference herein.

SUMMARY OF THE PRESENT INVENTION

The air convective warmer of the instant invention is an improvement of the existing EQUATOR® air warmer manufactured by the assignee of the instant application. Instead of reconfiguring the construction of the air warmer, the inventors found that by disrupting the air flow pattern in the air filter, the noise of the machine which presumably results from the blower and the air stream passing through the housing of the warmer, could be substantially reduced. Thus, instead of having to modify the whole machine, only the air filter of the air convective warmer needs to be reconfigured, thereby enabling the manufacturing of an airwarmer with a reduced noise level. So, too, the noise level of air warmers that are already in service can be readily reduced by simply retrofitting those warmers with the inventive air filter.

The inventive air filter has a base onto which an air filtering material is mounted. The filtering material extend upwards circumferentially from the base to form a circumferential wall, the top of which is capped by a cover that has an opening so that it looks as if there is a "donut hole" in the interior of the air filter, when the air filter is viewed from the top. It is through the top opening that air, sucked in through and filtered by the circumferential filtering material wall of the filter in the interior of the air filter, passes to the air blower of the warmer.

The filter is positioned adjacent to the air inlet of the convective warmer so that the incoming air is input to the machine through the filtering material of the filter. The filtered air, upon passing through the filtering material, arrives at the interior of the air filter and from there passes through the top opening to the heating element, or the air conditioning unit, where the temperature of the incoming air is effectively altered to colder or warmer air. From there, assuming that the air conditioning unit is a heater for the remainder of the disclosure, by means of the blower, the heated air is output to the air outlet of the warmer for inflating a convective blanket connected to the warmer.

To disrupt the flow of air from the filter to the plenum of the warmer, a first embodiment of the instant invention provides for the placement of at least one partition inside the interior of the air filter so that the volume of space in the interior of the air filter is divided. By empirical study, it was found that the optimal reduction of noise, from approximately 55.6 decibel to approximately 44.1 decibel for the EQUATOR® air warmer for example, is achieved when three partitions are placed into the interior of the filter, with each partition extending from the base of the filter to substantially the top opening of the filter. It was found that the efficiency of the air flow output by the air blower is not decreased. The optimal number of partitions may of course be dependent on the size of the machine, as well as the filter itself, and therefore may vary—be more or less than the mentioned three partitions—dependent on the machine and the filter used for the particular machine.

A second embodiment for interrupting the flow of air in the filter is by means of sealing the top opening of the filter, and extending through the sealed cover at least one open ended tube into the interior of the filter. The end of the tube that is extended into the filter is spatially separated from the base of the filter so that air may pass from the interior of the filter to the air plenum of the warmer through the open-ended tube. By providing a plurality of open-ended tubes, it was found that the air flow in the interior of the filter is disrupted in such a way that the noise level generated by the warmer is substantially reduced, and yet at the same time, the strength of the air stream flow from the warmer is not reduced, so that the efficiency with which the air warmer inflates the convective blanket connected thereto is not affected.

The air flow from the filter may also be interrupted by the covering of a portion of the filtering material by an air impermeable material, for example, a piece of plastic, so that the air input to the interior of the air filter passes into the air filter from only one portion of the filtering material. Further, for the air filter with the partition(s), the air flow is interrupted by having to go around the air filter between the partitions and the filter material and through the filter material into the interior of the filter. The inventors found that to be optimum, approximately ¼ to ¾, and preferably approximately 55%, of the filtering material be covered by the air impermeable material to both reduce the noise level and to continue to maintain the effectiveness of the air output from the air warmer.

The instant invention therefore relates to an apparatus for outputting temperature regulated air to an inflatable blanket at a reduced noise level that comprises a housing having an air inlet and an air outlet, an air conditioning unit, a blower for directing air from the air inlet to the air conditioning unit and from there to the air outlet to inflate the blanket, and an air filter interposed between the air inlet and the air outlet to filter the air from the air inlet, with the air filter having fitted thereto air intercept mechanism for interrupting the flow of air traversing through the air filter to the blower to thereby reduce the noise generated by the flow of forced air in the housing and attributable to at least the air blower.

The air intercept mechanism may be in the form of at least one partition positioned inside the interior of the air filter, with the partition(s) extending from the base to substantially the air output opening of the air filter. The air intercept mechanism may also comprise a cover that seals the opening of the air filter to the plenum of the air warmer, and at least one open-ended tube that extends from the cover into the interior of the air filter so that the air in the interior of the air filter is output through the tube to the plenum of the air warmer. The intercept mechanism may also comprise an air impermeable material shaped to cover a portion or portions of the circumferential surface of the filtering material of the air filter so that air from the air inlet passes into the interior of the air filter only through the portion(s) of the filtering material that is not covered by the air impermeable material.

The instant invention is also related to an air warmer for outputting temperature regulated air to an inflatable convective blanket that comprises: a housing having an air inlet and an air outlet; an air conditioning unit; a blower for directing air from the air inlet to the air conditioning unit and from there to the air outlet to inflate the blanket; at least one temperature sensor for sensing the temperature of air at the air outlet; an air filter interposed between the air inlet and the air outlet to filter the air from the air inlet, with the air filter having a base, an interior surrounded by a filtering material and an opening that allows air passing through the filtering material into the interior of the air filter to be routed to the air conditioning unit and the blower; and an air intercept mechanism fitted to the air filter for disrupting the flow of air traversing through the air filter to the blower.

The instant invention also relates to the method of reducing noise in an air convective warmer that has a housing having an air inlet and an air outlet, a blower to direct the air input from the air inlet to the air outlet, and an air conditioning unit to treat the air input from the air inlet so that temperature regulated air is output from the air outlet to inflate a convective blanket connected thereto. The method in particular recites the step (a) of positioning an air filter in the housing between the air inlet and the air outlet so that air from the air inlet passes through the air filter, and the step (b) of fitting to the air filter an air intercept mechanism for disrupting the flow of air in the air filter being routed to the air conditioning unit and the blower.

BRIEF DESCRIPTION OF THE FIGURES

The present invention will become apparent and the invention itself will be best understood with reference to the following description of the invention taken in conjunction with the accompanying drawings, wherein:

FIG. 2 shows a prior art air filter;

FIG. 3 shows the air filter of the instant invention;

FIG. 5a is an illustration of a second embodiment of the inventive air filter of the instant invention;

DETAILED DESCRIPTION OF THE INVENTION

Figure 1:
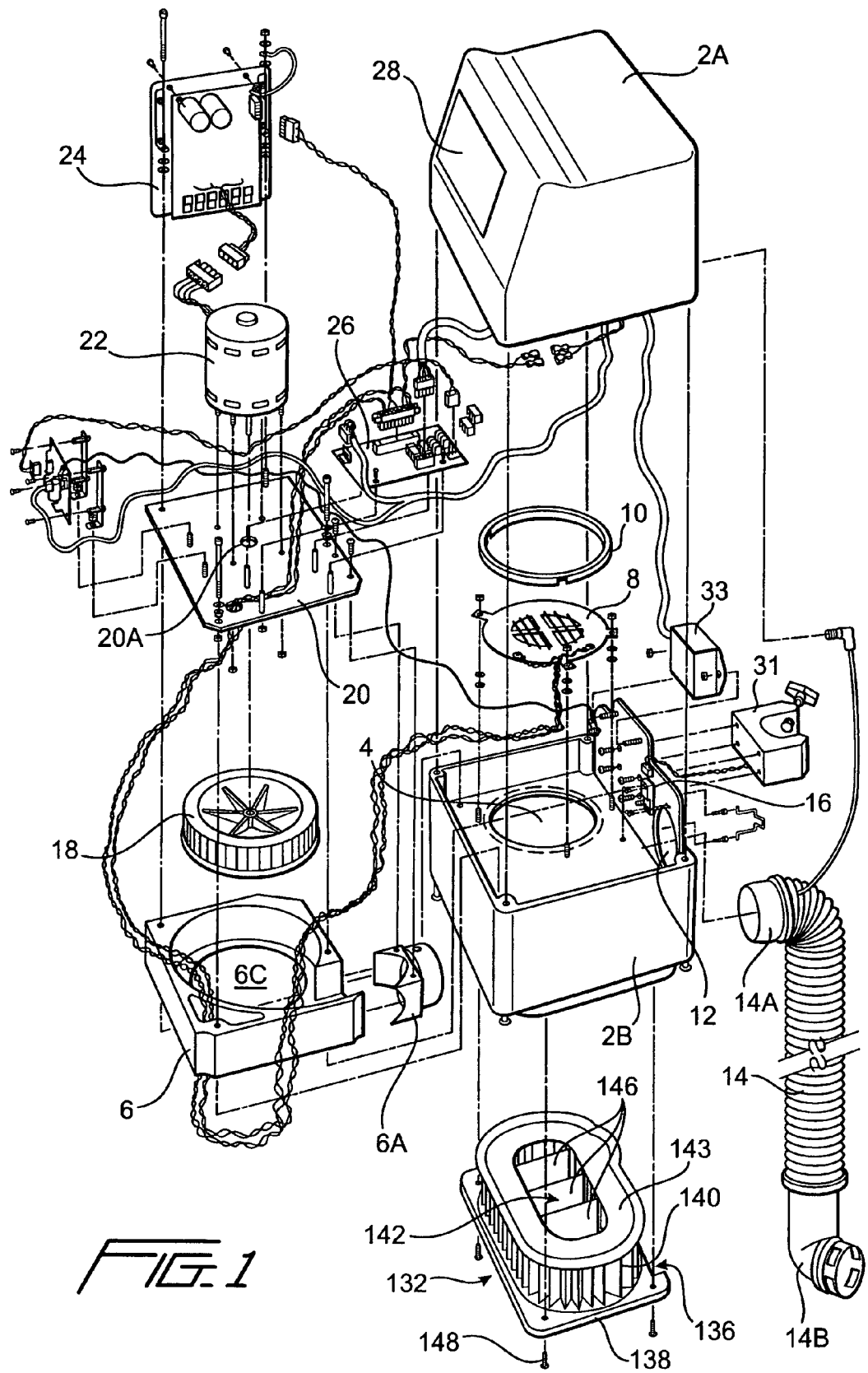
FIG. 1 is an exploded overall view of the air warmer of the instant invention, with the various components of the air warmer shown.

With reference to exploded view of FIG. 1, the air convective warmer of the instant invention is shown to include a housing that is made up of an upper part 2a and a lower part 2b. Lower housing 2b has an opening 4 onto which an air plenum 6 is fixedly positioned over, by means of shown screws. Although air plenum 6 is shown to be in two parts, with air outlet 6a being separate from the body proper of the air plenum, it should be appreciated that air plenum 6 could in fact be made of a one-piece construction, with the air outlet 6a being an integral part of the main body of the air plenum. Positioned between opening 4 and air plenum 6, at the latter's opening 6c, is a heater 8, or an air conditioning unit, that is placed over opening 4 of housing 2b. A gasket 10 is placed between heater 8 and plenum 6, when air plenum 6 is assembled to the interior of housing 2b. Air outlet 6a is fitted to opening 12 at the back of housing 2b in such a way that the machine end 14a of an air hose 14 is connectable or matable to air outlet 6a. The blanket end 14b of hose 14 is configured to be connectable to a conventional air convective blanket, not shown. Whether there is a secured connection between air outlet 6a and hose inlet 14a is determined by a micro switch sensor 16 mounted to the back of housing 2b.

An impeller, or blower fan 18 is positioned within the cavity of air plenum 6. Impeller 18, which is a part of the air blower of the air convective warmer, is mounted to a motor mounting plate 20, which in turn has mounted on its upper side a motor 22 whose drive shaft is connected to impeller 18 through an opening 20a provided at plate 20. Motor 22 is controlled by the electronics on motor driver board 24, which is mounted to motor mounting plate 20. Additional electronics are provided in a control panel (not shown as it is mounted within upper housing 2a), so that the speed with which impeller 18 is driven, as well as power provided to heater 8 to vary the temperature that heats the air input to the air blower, at air plenum 6, may be controlled. Further, the control panel controls the readouts and other indications provided at display 28 of housing 2a. The power supplied to the different components are provided by the power distribution board 26. The voltage used is controlled by mains filter 33. Various other electrical connections for the air warmer are also shown. They are not discussed herein insofar as the operation of a conventional air convection warmer is well known and need not be further discussed. The temperature of the air at the outlet/hose end of air hose 14 may be sensed by a sensor (not shown) provided at the outlet/hose end, which outputs a feedback signal to the control panel, so that feedback control may be provided to regulate the temperature of the air output from the air convective warmer to inflate or maintain the inflation of the convention blanket. Pole support part 31 is provided to the back of housing 2b to enable the air convective warmer to be mounted to a pole.

Prior to the instant invention, an air filter 32, such as that shown in FIG. 2, is mounted to the underside of housing 2b, per shown at upper corner view 34 of the figure, so that air is input to the air filter by way of slot or channel 36. Channel 36 may be referred to as the air inlet for the air warmer of FIG. 1. Air filter 32 has a base 38 onto which a filtering material 40 circumferentially extend upwards to form a substantially donut shaped hole, otherwise referred to as the interior 42 of the filter. A cover 43 caps the top of the filtering material 40 to effect an opening 44 at the top of the filtering material. It is through opening 44 that the air in the interior 42 of filter 32 that has passed through and been filtered by filtering material 40 is output to housing 2b, more specifically to the cavity of air plenum 6. Air filter 32 is fitted to the base of housing 2b, as shown by view 34.

With the air filter of FIG. 2, the air convection blower such as that shown in FIG. 1 works efficiently. However, it also produces a noise level that may be deemed high by some patients and/or users. One measurement of the noise generated by an air convective warmer fitter with the air filter of FIG. 2 was 55.6 decibels. Most of the noise generated by the air blower is due to the movement of the air blower, more specifically the impeller 18, as it is being driven by motor 22, and the flow of the air stream from air inlet 36 through air filter 32, and from there through air outlet 6a to air hose 14 to inflate and/or maintain the inflation of the convective blanket (not shown) connected to the air hose 14.

The inventors have discovered that by disrupting the air flow in interior 42 of air filter 32, the noise level generated by the air convective warmer may be substantially reduced. To achieve this disruption of air flow, a first embodiment of a modified air filter to be used the in the air convective warmer of FIG. 1 is shown in FIG. 3. As shown, air filter 132, like the air filter of FIG. 2, has a base 138 to which a filtering material 140 extends circumferentially to form an enclosed cavity 142 wherein ambient air passes from air inlet 136 through filtering material 140. An opening 144 is provided at air filter 132 for the filtered air in cavity 142 to be routed to housing 2b, and more specifically the cavity of air plenum 6, as indicated by its opening 6c. The filter material 140 is held in place by glue or other adhesive to base 138, and a top rim or cover 143 is attached to or covers the top of the filtering material to form the opening 144.

The inventors have found that by fitting the air filter with an air flow interrupt mechanism, the noise level of the air convective warmer may be reduced. For the embodiment of the air filter of FIG. 3, the air flow interrupt mechanism of the air filter comprises at least one partition 146 being positioned in the interior 142 of the air filter to disrupt the air flow routed from the environment to the air plenum of the housing of the air convective warmer. Such disruption in fact causes the noise level of the air convective warmer to be lowered. By empirical study, it was found that for the size and dimension of the air filter shown in FIG. 3, which is to be used with the air convective warmer of FIG. 1, an air disrupt mechanism that comprises three partitions 146a-146c positioned within interior 142 of the air filter provide the optimum result. This is not to say that a fewer or a higher number of partitions would not work just as well. A measurement taken with the placement of three partitions in the interior of the air filter of FIG. 3 shows that the noise level is reduced from the previously mentioned 55.6 decibels to approximately 44.1 decibels during the operation of the air convective warmer fitted with the inventive filter. As shown in the upper corner diagram 134 of FIG. 3, air filter 132 is mounted to the bottom of housing 2b by means of four screws 148.

Figure 4:
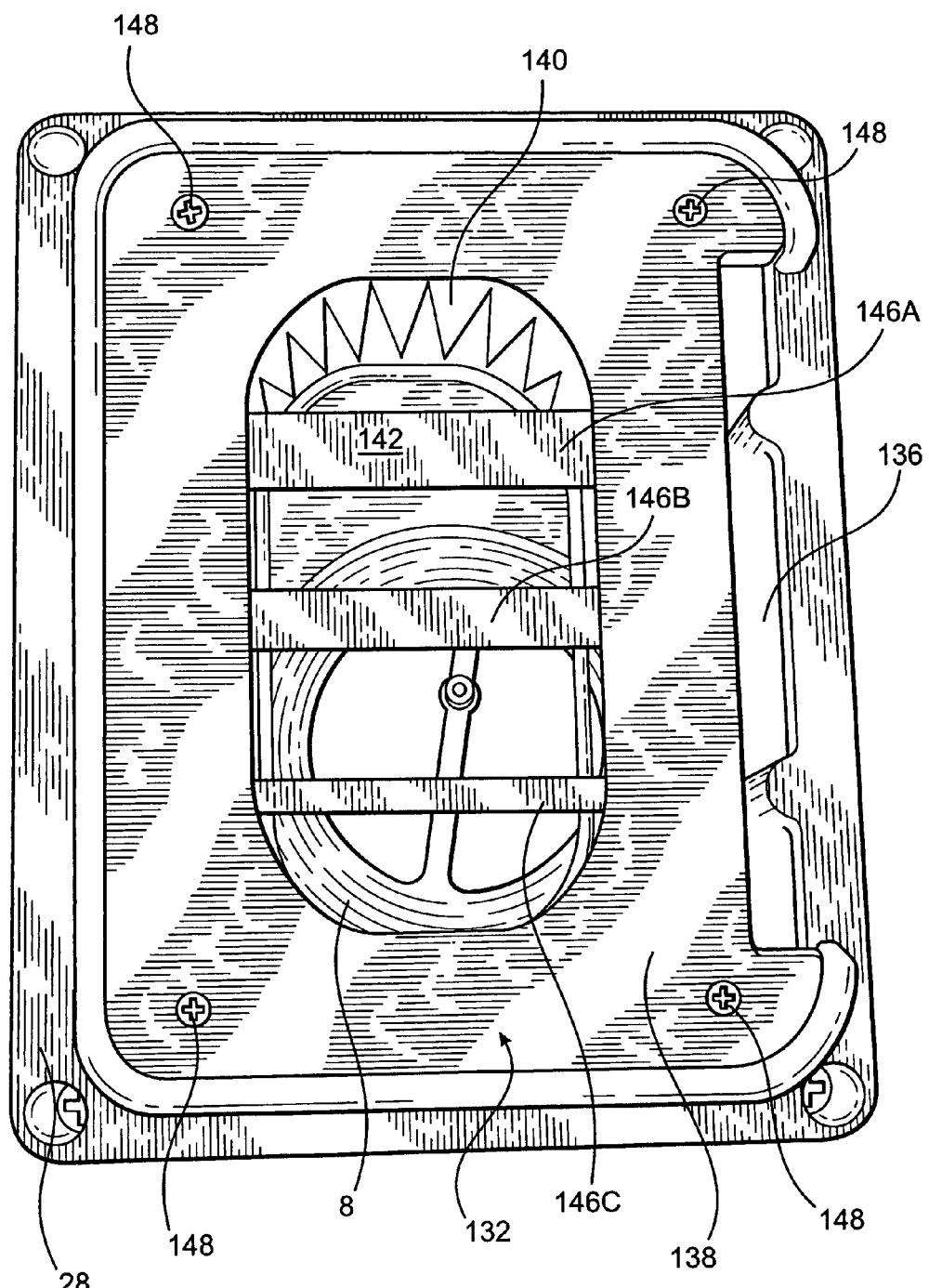
FIG. 4 shows a bottom view of the air warmer of the instant invention in which a portion of the base of the air filter of FIG. 3 has been removed to illustrate the placement of the partitions of the air filter of FIG. 3 relative to the heater and the opening to the plenum of the air warmer.

FIG. 4 shows the bottom view of the air convective warmer, particularly its housing portion 2b to which base 138 of air filter 132 is coupled by means of screws 148. For demonstration purposes, a portion of base 138 has been cut out to show the interior or cavity 142 of the air filter 132, and the partitions 146a to 146c which divide the volume of the interior space 142 of the air filter into three substantially equal portions. Note that the air filter is positioned underneath opening 4, to which heater 8 superposes over. Thus, as air from the environment is input to the air convective warmer through air inlet 136 due to the suctioning effect of impeller 18, the sucked in air passes through the filtering material 140 into interior cavity 142 of the air filter. Due to partitions 146, the air flow within the interior cavity of the air filter is disrupted. And it was found that such disrupted air flow actually reduces the noise of the flow of the air stream through air plenum 6, as well as the sound produced by the blower, as the intake air passes heater 8 it is warmed, and then is routed to air outlet 12. At the same time, the amount of air as well as the efficiency with which the warmed air output by the air convective warmer of the instant invention to inflate a convective blanket connected to the air warmer are determined not to be affected by the air filter fitted with the air interrupt mechanism.

Figure 5B:
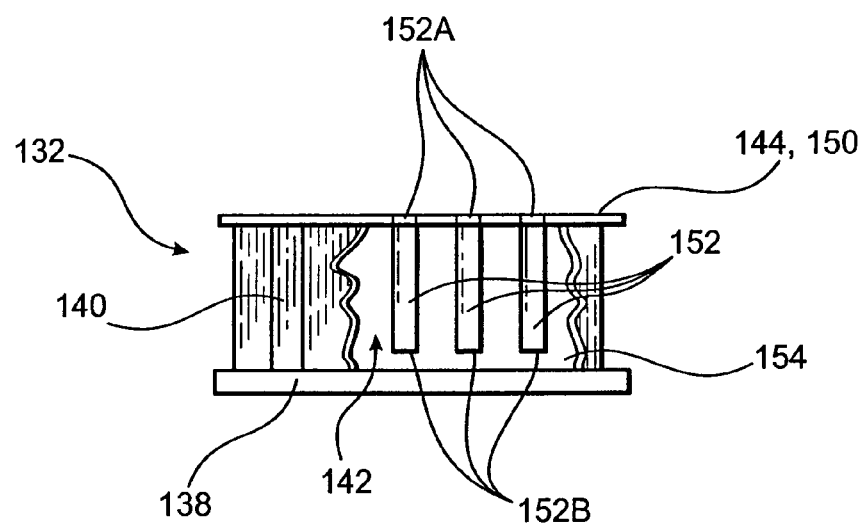
FIG. 5b is a semi cross-sectional exposed view of the FIG. 5a filter showing the positioning of the tubes in the interior space of the air filter.

A second embodiment of the noise reduction air filter of the instant invention is shown in FIGS. 5a and 5b. The same components for the FIG. 5 embodiment as those shown in the FIG. 3 embodiment are labeled the same. As shown, the opening of air filter 132, which is formed by rim 143, is sealed by a cover 150. The interior cavity 142 of air filter 132, as best shown in FIG. 5b, is thereby enclosed, except for channels that are created by a plurality of open-ended tubes 152. Respective first open ends of tubes 152 are attached to cover 150 to thereby provide openings or apertures 152a to the opening 4 of housing 2b and also therefore the internal cavity 6c of air plenum 6. The other respective open ends of tubes 152, designated 152b in FIG. 5b, are spatially separated from base 138 by a predetermined distance 154, so that the filtered air in cavity 142 of air filter 132 passes through open ends 152b of the open-ended tubes 152 and from there passes into cavity 6c of air plenum 6 by way of openings 152a, after being warmed by heater 8. The inventors found that the air filter shown in the embodiment of FIG. 5 works equally well in reducing the noise of the air convective warmer, as tubes 152 would disrupt the air flow from air filter 132 to air plenum 6, and yet at the same time not affecting the amount of warmed air output from the air convective warmer to inflate the convective blanket connected thereto. Note that even though six tubes 152 are shown, a smaller or a greater number of tubes may be used for the FIG. 5 embodiment to reduce the noise level of the air convective warmer of the instant invention.

Figure 6:
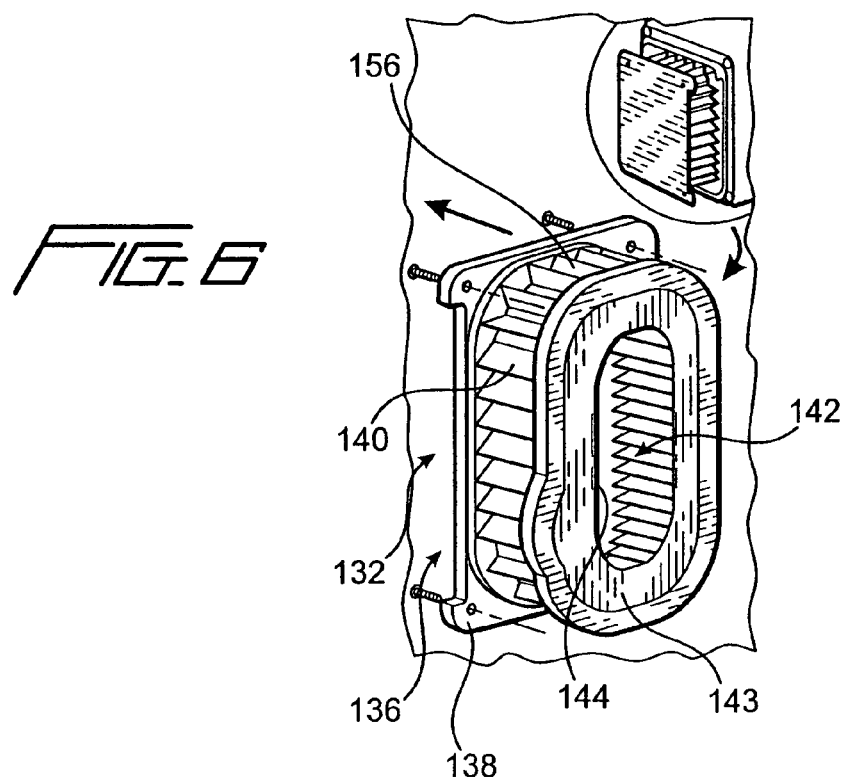
FIG. 6 shows another embodiment of the air filter of the instant invention in which a portion of the filtering material of the filter is covered by an air impermeable material.

Another embodiment of the noise reduction air filter of the instant invention is shown in FIG. 6. For this embodiment, to disrupt the air flow inside the interior cavity 142 of air filter 132, an air impermeable material 156, such as plastic, is wrapped about a portion of the circumferential surface of the filtering material 140. Although shown as wrapping around the outside circumferential surface of filtering material 140 in FIG. 6, it should be appreciated that the air impermeable material 156 may in fact be placed against the inside circumferential surface of filtering material 140 from within the interior cavity of air filter 132. So long as the air impermeable material prevents the air from the environment from passing directly or orthogonally from all external directions through the filtering material 140 into the interior cavity 142 of air filter 132, it was found that the air flow inside the air filter is disrupted. As shown in FIG. 6, by blocking at least one portion, or portions, of filtering material 140 with the air impermeable material 156, the ambient air is prevented from passing directly or orthogonally through the covered portion of the external surface of the filtering material 140 into air filter 132. By empirical studies, the inventors found that an optimal reduction of the noise level of the air convective warmer may be gained by covering approximately over one half of the surface area of the filtering material 140 of the air filter, either circumferentially at the external surface as shown or internally at the internal surface of the filtering material. The noise level of the air convective warmer nonetheless may be reduced even were the surface area of the filtering material 140 covered from approximately 40% to 60%, instead of the optimal over one-half surface area noted above.

In operation, once the air convective warmer is properly connected to the air convective blanket by means of air hose 14, upon activation of the air convective warmer, due to the rotation of blower impeller 18, ambient air is sucked in from air inlet 136 and passes into the interior cavity 142 of air filter 132 through the filtering material 140. Due to the disruption of the air flow in the interior cavity 142 of the air filter 132, the air that passes heater 8 and sucked into cavity 6c of air plenum 6 due to the rotation of impeller 18 does not generate as much noise as when there is no disruption to the airflow. The amount of air output from the air convective warmer to the convective blanket, however, remains substantially unaffected by the interruption to the air flow so the the efficiency of the air convective warmer is not decreased.

The invention claimed is:

1. Apparatus for outputting temperature regulated air to an inflatable blanket at a reduced noise level, comprising:
   a housing having an air inlet and an air outlet;
   an air conditioning unit;
   a blower for directing air from said air inlet to said air conditioning unit and from there to said air outlet to inflate the blanket; and
   an air filter interposed between said air inlet and said air outlet to filter the air from said air inlet, said air filter having a base and a filtering element extending circumferentially from the base to form an enclosed interior cavity wherein air intercept means is fitted for disrupting the flow of air traversing in the interior cavity of said air filter as the filtered air is provided to said air conditioning unit, whereby noise generated by the flow of forced air in said housing and attributable to at least said blower is reduced.

2. Apparatus of claim 1, wherein said air filter comprises an opening to its interior cavity wherefrom air is routed to said air conditioning unit, the interior cavity of said air filter surrounded by a filtering material through which air from said air inlet passes into the interior of said air filter; and wherein said air intercept means comprises at least one partition positioned in the interior cavity of said air filter to divide the volume of space in the interior cavity of said air filter.

3. Apparatus of claim 1, wherein said air filter comprises a base and a filtering material surrounding said air filter with an opening wherefrom air passing the filtering material into the interior cavity of said air filter from said air inlet is routed to said air conditioning unit; and wherein said air intercept means comprises at least one partition extending from the base in the interior cavity of said air filter.

4. Apparatus of claim 1, wherein said air filter comprises a base and a filtering material surrounding said air filter with an opening wherefrom air passing the filtering material into the interior cavity of said air filter from said air inlet is routed to said air conditioning unit; and wherein said air intercept means comprises three partitions extending within the interior cavity from the base towards the opening of said air filter.

5. Apparatus of claim 1, wherein said air filter comprises a base and a filtering material surrounding said air filter with an opening wherefrom air passing the filtering material into the interior of said air filter from said air inlet is routed to said air conditioning unit; and wherein said air intercept means comprises a cover sealing the opening of said air filter and at least one open-ended tube that extends from said cover into the interior of said air filter so that air in the interior of said air filter is output through said tube.

6. Apparatus of claim 5, wherein the end of said open-ended tube that extends into the interior of said air filter is spatially separated from the base of said air filter.

7. Apparatus of claim 1, wherein said air filter comprises a base and a filtering material surrounding said air fitter with an opening wherefrom air passing the filtering material into the interior of said air filter from said air inlet is routed to said air conditioning unit; and wherein said air intercept means comprises an air impermeable material shaped to cover at least one portion of the surface of the filtering material so that air from said air inlet is prevented from passing directly through the covered surface of the air filtering material into the interior of said air filter.

8. Apparatus of claim 7, wherein the portion of the circumferential surface of said air filter covered by said air impermeable material faces at least said air inlet.

9. An air warmer for outputting temperature regulated air to an inflatable convective blanket, comprising:
   a housing having an air inlet and an air outlet;
   a heater;
   a blower for directing air from said air inlet to said heater and from there to said air outlet to inflate the blanket;
   at least one temperature sensor for sensing the temperature of the air output to inflate the blanket;
   an air filter interposed between said air inlet and said air outlet to filter the air from said air inlet, said air filter having a base, an interior cavity surrounded by a filtering material extending from the base and an opening that allows air passing through the filtering material into the interior of said air filter to be routed to said heater and said blower; and
   air intercept means fitted within the interior cavity of said air filter for disrupting the flow of air traversing in the interior cavity of said air filter and passes to said blower.

10. Air warmer of claim 9, wherein said air intercept means comprises at least one partition positioned in the interior cavity of said air filter to divide the volume of space inside the interior cavity of said air filter.

11. Air warmer of claim 9, wherein said air intercept means comprises at least one partition extending within the interior cavity of said air filter from the base to the opening of said air filter.

12. Air warmer of claim 9, wherein said air intercept means comprises three partitions extending within the interior cavity of said air filter from the base to the opening of said air filter.

13. Air warmer of claim 9, wherein said air intercept means comprises a cover sealing the opening of said air filter and at least one open-ended tube that extends from said cover into the interior of said air filter so that air in the interior of said air filter is output through said tube.

14. Air warmer of claim 13, wherein the end of said open-ended tube that extends into the interior of said air filter is spatially separated from the base of said air filter.

15. Air warmer of claim 9, wherein said air intercept means comprises an air impermeable material shaped to cover at least one portion of the surface of the filtering material so that air from said air inlet is prevented from entering into the interior of said air fitter directly through the covered surface of the filtering material.

16. In an air warmer having a housing including an air inlet and an air outlet, a blower to direct the air input from said air inlet to said air outlet, and a heater to heat air input from said air inlet so that a temperature regulated air is output from said air outlet to inflate a convective blanket connected thereto, a method of reducing noise produced by the air warmer comprising the steps of:
   a) positioning an air filter in said housing between said air inlet and said air outlet so that air from said air inlet passes through said air filter, said air filter having a base, an interior cavity surrounded by a filtering material extending from the base and an opening that allows air passing through the filtering material into the interior cavity of said air filter to be routed to said heater; and
   b) fitting to the interior cavity of said air filter air intercept means for disrupting the flow of air in the interior cavity of said air filter being routed to said heater.

17. Method of claim 16, wherein said step b further comprises the step of:
   positioning at least one partition within the interior cavity of said air filter.

18. Method of claim 16, wherein said step b further comprises the steps of:
   positioning three partitions within the interior cavity of said air filter; and
   extending said partitions within the interior cavity of said air filter from the base to substantially the opening of said air filter.

19. Method of claim 16, wherein said step b further comprises the steps of:
   sealing the opening of said air filter with a cover; and
   extending from said cover into the interior of said air filter at least one open-ended tube so that air in the interior of said air filter is output through said tube.

20. Method of claim 16, wherein said step b further comprises the step of:
   covering at least one portion of the surface of the filter material with an air impermeable material so that air from said air inlet is prevented from entering into the interior of said air filter directly through the covered surface of the filtering material.

* * * * *